(12) United States Patent
Hwang et al.

(10) Patent No.: US 10,550,137 B2
(45) Date of Patent: Feb. 4, 2020

(54) STABILIZER FOR PRODUCING A POLYESTER RESIN, PROCESS FOR PREPARING THE SAME, PROCESS FOR PRODUCING THE POLYESTER RESIN USING THE SAME, AND THE POLYESTER RESIN PRODUCED THEREBY

(71) Applicant: Far Eastern New Century Corporation, Taipei (TW)

(72) Inventors: Der-Ren Hwang, Taipei (TW); Hsin-Hui Cheng, Taipei (TW)

(73) Assignee: Far Eastern New Century Corporation, Taipei (TW)

( * ) Notice: Subject to any disclaimer, the term of this patent is extended or adjusted under 35 U.S.C. 154(b) by 34 days.

(21) Appl. No.: 15/907,220

(22) Filed: Feb. 27, 2018

(65) Prior Publication Data
US 2019/0106444 A1   Apr. 11, 2019

(30) Foreign Application Priority Data

Oct. 5, 2017 (TW) .............................. 106134348 A

(51) Int. Cl.
*C07F 9/12* (2006.01)
*C08K 5/523* (2006.01)
(Continued)

(52) U.S. Cl.
CPC .............. *C07F 9/12* (2013.01); *C07F 9/091* (2013.01); *C08G 63/6926* (2013.01);
(Continued)

(58) Field of Classification Search
CPC . C07F 9/12; C07F 9/091; C08G 63/80; C08G 63/82; C08K 5/523
(Continued)

(56) References Cited

U.S. PATENT DOCUMENTS 6,384,180 B1 *  5/2002  Jernigan .............. C08G 63/866
                                                      524/115

OTHER PUBLICATIONS

Shuzo Sawada, et al., "Degradation Mechanisms of Poly (ethylene Terephthalate) Tire Yarn", Journal of Applied Polymer Science, vol. 42, 1041-1048 (1991).

* cited by examiner

*Primary Examiner* — William K Cheung
(74) *Attorney, Agent, or Firm* — Lowe Graham Jones PLLC

(57) ABSTRACT

A stabilizer for producing a polyester resin comprises a phosphate ester composition which includes a phosphate ester compound having Formula (I),

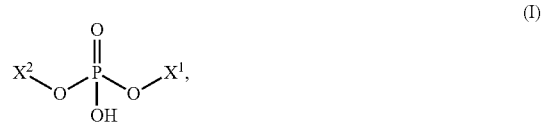

wherein
$X^1$ represents

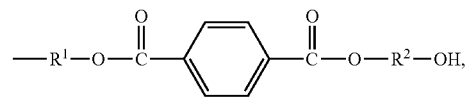

and
$X^2$ represents H or (Continued)

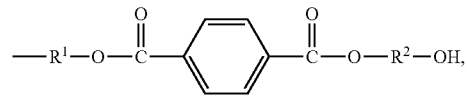
wherein
R¹ and R² are independently selected from the group consisting of a linear $C_2$-$C_4$ alkylene group, a branched $C_3$-$C_4$ alkylene group, and a combination thereof.
10 Claims, 2 Drawing Sheets
(51) Int. Cl.
*C08G 63/82* (2006.01)
*C08G 63/80* (2006.01)
*C08G 63/85* (2006.01)
*C08G 63/692* (2006.01)
*C07F 9/09* (2006.01)
(52) U.S. Cl.
CPC ............ *C08G 63/80* (2013.01); *C08G 63/82* (2013.01); *C08G 63/85* (2013.01); *C08K 5/523* (2013.01)
(58) Field of Classification Search
USPC ....................................................... 524/127
See application file for complete search history.

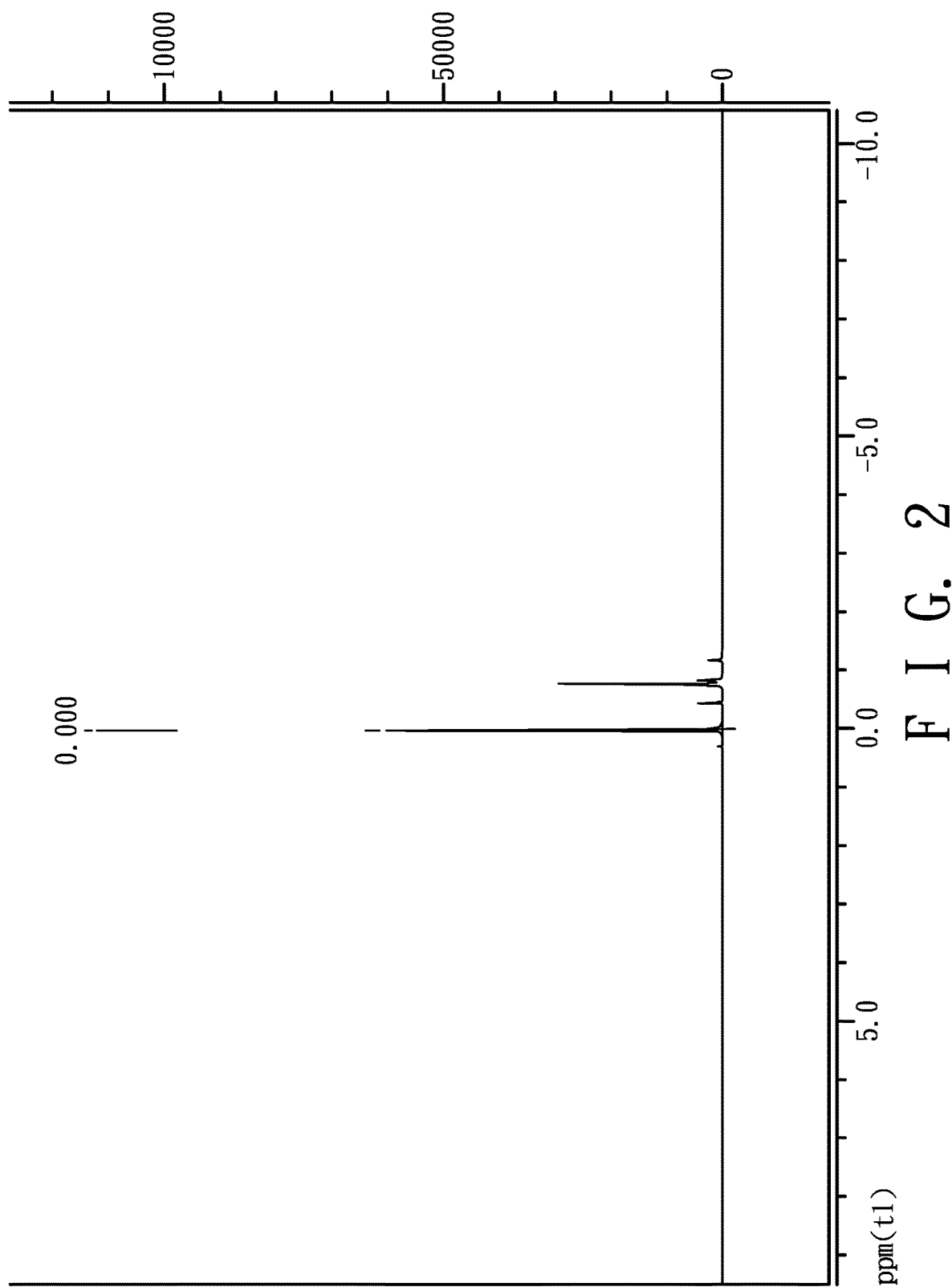

STABILIZER FOR PRODUCING A POLYESTER RESIN, PROCESS FOR PREPARING THE SAME, PROCESS FOR PRODUCING THE POLYESTER RESIN USING THE SAME, AND THE POLYESTER RESIN PRODUCED THEREBY

CROSS-REFERENCE TO RELATED APPLICATION

This application claims priority of Taiwanese Application No. 106134348, filed on Oct. 5, 2017.

FIELD

The disclosure relates to a stabilizer, and more particularly to a stabilizer for producing a polyester resin. The disclosure also relates to a process for preparing the stabilizer, a process for producing the polyester resin using the stabilizer, and the polyester resin produced thereby.

BACKGROUND

In conventional processes for producing a polyester resin, a polycondensation reaction is usually performed in the presence of a metal-containing catalyst so as to enhance the reaction rate. However, the presence of the metal-containing catalyst may cause undesirable degradation of the polyester resin produced such that the polyester resin may have problems such as an insufficient molecular weight and an inferior color.

In order to solve the aforesaid problems, a phosphorus-containing additive (e.g., phosphoric acid and derivatives thereof, phosphorous acid and derivatives thereof, and the like) is usually used as a stabilizer in the production of the polyester resin to inhibit the degradation of the polyester resin. However, the reaction rate of the polycondensation reaction may thus be decreased and the yield of the polyester resin may also be reduced accordingly.

U.S. Pat. No. 6,384,180 B1 discloses a process for making a polyester resin employing an acidic phosphorus-containing compound, such as phosphoric acid, phosphorous acid, polyphosphoric acid, acidic phosphate esters or mixtures thereof. It is also disclosed therein that when phosphoric acid is added to an esterification product containing antimony, the finisher time is increased significantly with increasing phosphorus level, and certain inorganic compounds such as antimony phosphate may be produced to cause particulate haze in the polyester resin. Furthermore, use of a phosphate triester as a phosphorus additive is also disclosed therein.

SUMMARY

A first object of the disclosure is to provide a stabilizer for producing a polyester resin to solve the aforesaid problems, such as degradation of the polyester resin, encountered in the prior art and to enhance thermal stability of the polyester resin in a further processing procedure.

A second object of the disclosure is to provide a process for preparing the stabilizer.

A third object of the disclosure is to provide a process for producing a polyester resin using the stabilizer.

A fourth object of the disclosure is to provide a polyester resin produced thereby.

According to a first aspect of the disclosure, there is provided a stabilizer for producing a polyester resin. The stabilizer comprises a phosphate ester composition which includes a phosphate ester compound having Formula (I),

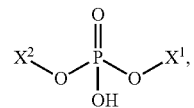
(I)

wherein
X$^1$ represents

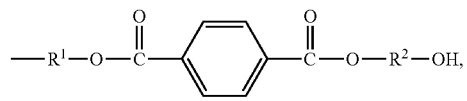

and
X$^2$ represents H or

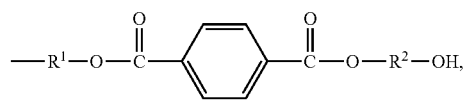

wherein
R$^1$ and R$^2$ are independently selected from the group consisting of a linear C$_2$-C$_4$ alkylene group, a branched C$_3$-C$_4$ alkylene group, and a combination thereof.

According to a second aspect of the disclosure, there is provided a process for preparing the stabilizer of the first aspect of the disclosure. The process comprises steps of:

a) dispersing a phosphating reagent in a solvent to obtain a phosphating reagent dispersion; and b) subjecting a compound having Formula (A) to a phosphorylation reaction by gradually adding the compound having Formula (A) into the phosphating reagent dispersion,

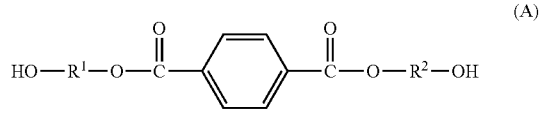
(A)

wherein
R$^1$ and R$^2$ are independently selected from the group consisting of a linear C$_2$-C$_4$ alkylene group, a branched C$_3$-C$_4$ alkylene group, and a combination thereof.

According to a third aspect of the disclosure, there is provided a process for producing a polyester resin, which comprises a step of subjecting a dicarboxylic ester component to a polycondensation reaction in the presence of a catalyst and the stabilizer of the first aspect of the disclosure.

According to a fourth aspect of the disclosure, there is provided a polyester resin produced by the process of the third aspect of the disclosure.

BRIEF DESCRIPTION OF THE DRAWINGS

Other features and advantages of the disclosure will become apparent in the following detailed description of the embodiment (s) with reference to the accompanying drawings, of which:

FIG. 2 is a $^{31}$P NMR spectrum for the stabilizer prepared in Preparation Example 1.

DETAILED DESCRIPTION

Figure 1:
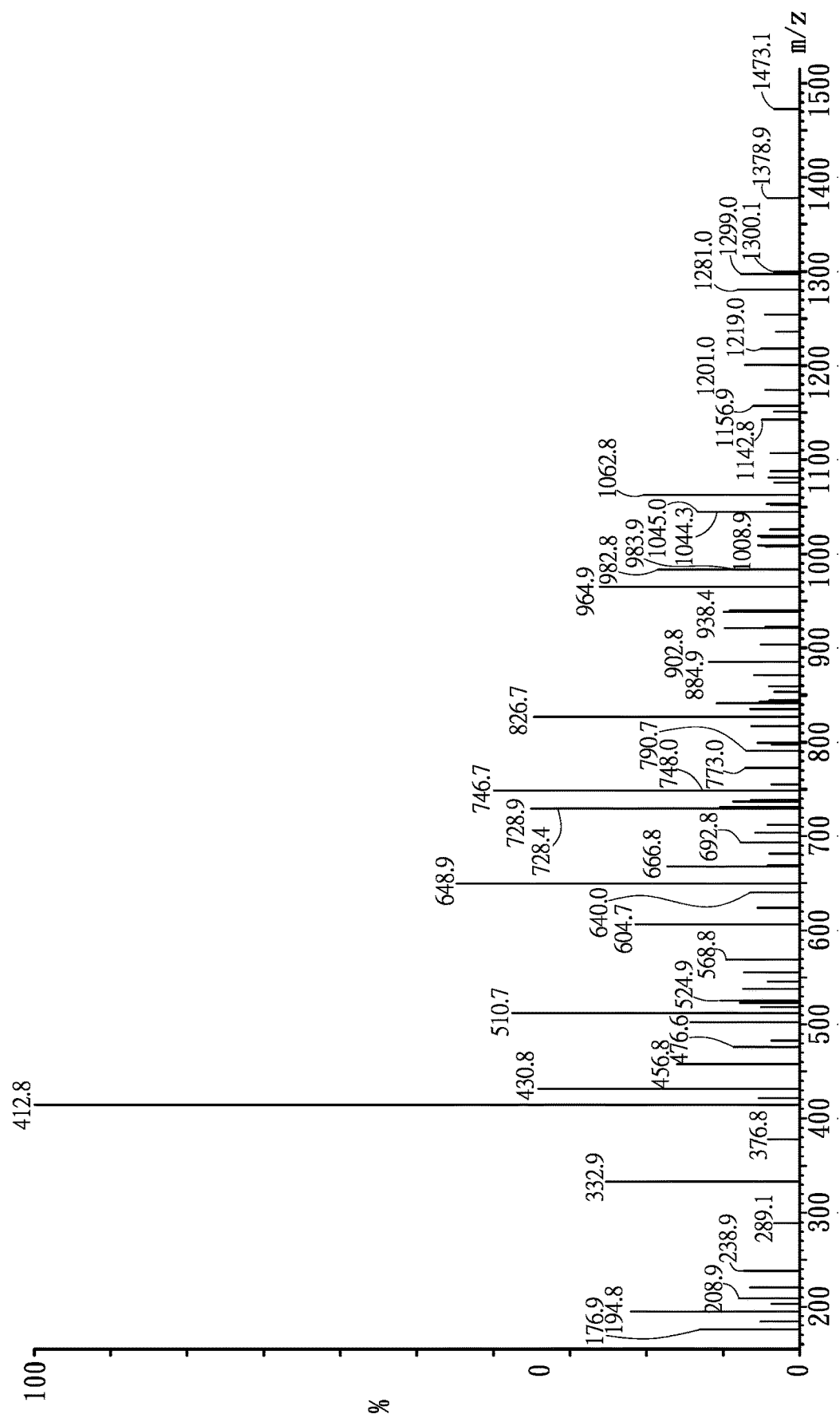
FIG. 1 is a spectrum of an electrospray ionization-mass spectrometry (ESI-MS) for a stabilizer prepared in Preparation Example 1.

A stabilizer for producing a polyester resin according to the disclosure comprises a phosphate ester composition which includes a phosphate ester compound having Formula (I),

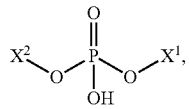

(I)

wherein
X$^1$ represents

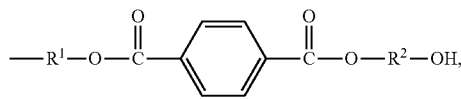

and
X$^2$ represents H or

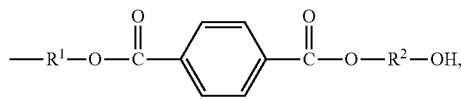

wherein
R$^1$ and R$^2$ are independently selected from the group consisting of a linear C$_2$-C$_4$ alkylene group, a branched C$_3$-C$_4$ alkylene group, and a combination thereof.

Examples of the linear C$_2$-C$_4$ alkylene group include ethylene, propylene, and n-butylene. Examples of the branched C$_3$-C$_4$ alkylene group include isopropylene, sec-butylene, isobutylene, and tert-butylene. In certain embodiments, R$^1$ and R$^2$ are ethylene.

In certain embodiments, the phosphate ester composition includes the phosphate ester compound having Formula (I) wherein X$^2$ is H, i.e., the phosphate ester compound having Formula (II),

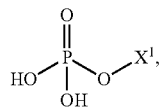

(II)

wherein X$^1$ is the same as that defined for Formula (I).

In certain embodiments, the phosphate ester composition includes a combination of the phosphate ester compound having Formula (I) wherein X$^2$ is H and the phosphate ester compound having Formula (I) wherein X$^2$ is

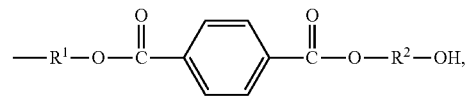

i.e., a combination of the phosphate ester compound having Formula (II) described above and the phosphate ester compound having Formula (III),

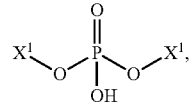

(III)

wherein X$^1$ is the same as that defined for Formula (I).

There is no specific limitation as to an equivalent ratio of the phosphate ester compound having Formula (II) to the phosphate ester compound having Formula (III) in the combination. In certain embodiments, in order to more effectively inhibit degradation of the polyester resin to be produced, the phosphate ester compound having Formula (II) and the phosphate ester compound having Formula (III) in the combination are in an equivalent ratio ranging from 1:1 to 9:1. In certain embodiments, the equivalent ratio of the phosphate ester compound having Formula (II) to the phosphate ester compound having Formula (III) in the combination is in a range from 3:1 to 9:1. It should be noted that the phosphate ester compound having Formula (II) is more effective in inhibiting degradation of the polyester resin to be produced than the phosphate ester compound having Formula (III). It should also be noted that the stabilizer of the disclosure may react with an end group of a dicarboxylic ester component for producing the polyester resin so as to inhibit degradation of the polyester resin to be produced.

A process for preparing the stabilizer according to the disclosure comprises steps of:

a) dispersing a phosphating reagent in a solvent to obtain a phosphating reagent dispersion; and b) subjecting a compound having Formula (A) to a phosphorylation reaction by gradually adding the compound having Formula (A) into the phosphating reagent dispersion,

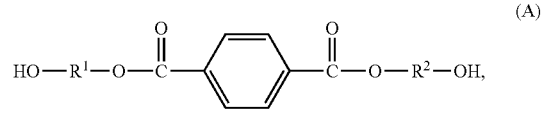

(A)

wherein R$^1$ and R$^2$ are the same as those defined for Formula (I). In certain embodiments, R$^1$ and R$^2$ are ethylene.

A non-limiting example of the compound having Formula (A) is bis(2-hydroxyethyl) terephthalate, which may be a commercially available reagent-grade chemical, or which may be obtained by an alcoholysis reaction of polyethylene terephthalate with ethylene glycol or by a reaction of terephthalic acid with ethylene oxide. It should be noted that the bis-hydroxy alkyl terephthalate used in the disclosure is a pure material, i.e., a compound of

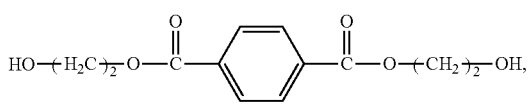

rather than a mixture of bis(2-hydroxyethyl) terephthalate and oligomer thereof obtained via an esterification reaction of terephthalic acid with ethylene glycol. The represented by Formula (B),

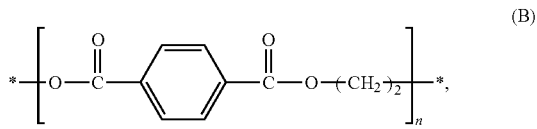

wherein n is an integer ranging from 2 to 16.

In certain embodiments, the phosphating reagent is selected from the group consisting of phosphoric acid, polyphosphoric acid, phosphorus pentoxide, and combinations thereof. In certain embodiments, the phosphating reagent is phosphorus pentoxide in view of the fact that residual phosphoric acid in the stabilizer thus prepared may be detrimental to a polycondensation reaction for producing the polyester resin if phosphoric acid is used as the phosphating reagent.

There is no specific limitation as to a molar ratio of the phosphating reagent to the compound having Formula (A). The molar ratio may be adjusted according to a desirable equivalent ratio of the phosphate ester compound having Formula (II) to the phosphate ester compound having Formula (III) in the stabilizer to be prepared. In certain embodiments, the molar ratio of the phosphating reagent to the compound having Formula (A) is in a range from 1:1 to 1:2 in view of the fact that the equivalent ratio of the phosphate ester compound having Formula (II) to the phosphate ester compound having Formula (III) in the stabilizer to be prepared is at least 1 so as to more effectively inhibit degradation of the polyester resin to be produced. In certain embodiments, the molar ratio of the phosphating reagent to the compound having Formula (A) is in a range from 1:1.1 to 1:1.5.

There is no specific limitation as to the reaction conditions for the phosphorylation reaction. For example, the phosphorylation reaction may be performed at a temperature ranging from 40° C. to 100° C. for a period ranging from 1 hour to 5 hours.

A process for producing a polyester resin according to the disclosure comprises a step of subjecting a dicarboxylic ester component to a polycondensation reaction in the presence of a catalyst and the stabilizer of the disclosure.

The dicarboxylic ester component includes at least one dicarboxylic ester-based substance which may be a product obtained by subjecting a dicarboxylic acid compound and a diol compound to an esterification reaction or a product obtained by subjecting a dialkyl dicarboxylate compound and a diol compound to a trans-esterification reaction.

Examples of the dicarboxylic acid compound include, but are not limited to, aliphatic dicarboxylic acid compounds and aromatic dicarboxylic acid compounds. Examples of the aliphatic dicarboxylic acid compounds include, but are not limited to, cyclohexane dicarboxylic acid, succinic acid, glutaric acid, adipic acid, sebacic acid, 1,12-dodecane dioic acid, and itaconic acid, which may be used alone or in admixture of two or more thereof. Examples of the aromatic dicarboxylic acid compounds include, but are not limited to, $C_8$-$C_{12}$ aromatic dicarboxylic acid compounds, which may be used alone or in admixture of two or more thereof. Examples of the $C_8$-$C_{12}$ aromatic dicarboxylic acid compounds include, but are not limited to, terephthalic acid (TPA), isophthalic acid (IPA), phthalic acid, and 2,6-naphthalic acid. In certain embodiments, the dicarboxylic acid compound is selected from the group consisting of the aromatic dicarboxylic acid compounds.

Examples of the dialkyl dicarboxylate compound include, but are not limited to, dialkyl ester compounds of aliphatic dicarboxylic acids and dialkyl ester compounds of aromatic dicarboxylic acids. Examples of the dialkyl ester compounds of aliphatic dicarboxylic acids include, but are not limited to, dialkyl cyclohexanedicarboxylate, dialkyl succinate, dialkyl glutarate, dialkyl adipate, dialkyl sebacate, dialkyl dodecanedioate, and dialkyl methylene succinate, which may be used alone or in admixture of two or more thereof. Examples of the dialkyl ester compounds of aromatic dicarboxylic acids include, but are not limited to, dialkyl ester compounds of $C_{10}$-$C_{14}$ aromatic dicarboxylic acids, which may be used alone or in admixture of two or more thereof. Examples of dialkyl ester compounds of $C_{10}$-$C_{14}$ aromatic dicarboxylic acids include, but are not limited to, dialkyl terephthalate, dialkyl isophthalate, dialkyl phthalate, dialkyl 2,6-naphthalate, and dialkyl biphenyldicarboxylate. In certain embodiments, the dialkyl dicarboxylate compound is selected from the group consisting of the dialkyl ester compounds of aromatic dicarboxylic acids.

Examples of the diol compound include, but are not limited to, aliphatic diol compounds and aromatic diol compounds. Examples of the aliphatic diol compounds include, but are not limited to, $C_2$-$C_4$ aliphatic diol compounds, which may be used alone or in admixture of two or more thereof. Examples of the $C_2$-$C_4$ aliphatic diol compounds include, but are not limited to, ethylene glycol (EG), 1,3-propylene glycol, 1,2-propylene glycol, 1,3-butylene glycol, 1,4-butylene glycol, and 2,3-butylene glycol. Examples of the aromatic diol compounds include, but are not limited to, hydroquinone, resorcinol, and naphthalene glycol. In certain embodiments, the diol compound is selected from the group consisting of the aliphatic diol compounds.

In certain embodiments, in the polycondensation reaction for producing the polyester resin, in order to more effectively inhibit degradation of the polyester resin to be produced and not to cause a negative effect on the production rate and yield of the polyester resin to be produced, the stabilizer is used in an amount such that the polyester resin thus produced contains a practical phosphorus content in a range from 5 ppm to 150 ppm.

In certain embodiments, the catalyst for the polycondensation reaction is a metal-containing catalyst. Examples of the metal-containing catalyst include, but are not limited to, antimony-containing compounds, germanium-containing compounds, tin-containing compounds, titanium-containing compounds, gallium-containing compounds, and aluminum-containing compounds, which may be used alone or in admixture of two or more thereof. In certain embodiments, concrete examples of the metal-containing catalyst include, but are not limited to, antimony (III) oxide ($Sb_2O_3$), antimony acetate, antimony glycolate, titanium isopropoxide, titanium butoxide, germanium oxide, dibutyltin oxide, n-butyl hydroxytin oxide, and combinations thereof. There is no specific limitation as to the amount of the catalyst, which may be adjusted according to practical requirements.

In the polycondensation for producing the polyester resin, the polycondensation reaction is accompanied by a reaction of the stabilizer of the disclosure with an end group of a dicarboxylic ester component so as to inhibit degradation of the polyester resin to be produced.

There is no specific limitation as to the reaction conditions for the polycondensation reaction for producing polyester resin as long as the polycondensation reaction may be performed. In certain embodiments, the reaction temperature for the polycondensation reaction is in a range from 260° C. to 280° C.

Examples of the disclosure will be described hereinafter. It is to be understood that these examples are exemplary and explanatory and should not be construed as a limitation to the disclosure.

Preparation Example 1: Preparation of a Stabilizer

Into a reaction vessel was added 1,2-dichloroethane (100 ml), followed by addition and dispersion of phosphorus pentoxide ($P_2O_5$, 15.05 g, 0.105 mol) in 1,2-dichloroethane in the reaction vessel placed in an ice bath to obtain a phosphorus pentoxide dispersion. Bis(2-hydroxyethyl) terephthalate (Tokyo Chemical Industry Co., Product No. B3429) in a total amount of 29.9 g (0.118 mol) was added gradually into the reaction vessel, followed by a gradual raise of the temperature in the reaction vessel to 80° C. to subject bis(2-hydroxyethyl) terephthalate and phosphorus pentoxide to a phosphorylation reaction for 3 hours. Deionized water was then added into the reaction vessel in an amount which is determined according to a formula below and the phosphorylation reaction was continued for 1 hour at 70° C. and then terminated to obtain a coarse product. The coarse product was distillated under a reduced pressure to remove 1,2-dichloroethane to obtain a phosphate ester combination containing a phosphate monoester compound of Formula (I-1) and a phosphate diester compound of Formula (II-1), Amount of deionized water=(weight of bis(2-hydroxyethyl) terephthalate+weight of phosphorus pentoxide)×2%.

The phosphate ester combination was titrated using an aqueous solution of potassium hydroxide (0.1 M) to determine an equivalent ratio of the phosphate monoester compound of Formula (I-1) to the phosphate diester compound of Formula (II-1), which was found to be 3.3:1.

The phosphate ester combination was also analyzed using an electrospray ionization mass spectrometer (ESI-MS, Bruker, Impact HD, EVOQ) and a 31-P nuclear magnetic resonance spectrometer ($^{31}P$ NMR, Bruker, resonance frequency: 400 MHz, solvent: DMSO, $H_3PO_4$ was used as an internal standard at 0 ppm). It was confirmed from a spectrum of ESI-MS shown in FIG. 1 that the phosphate ester combination contained the phosphate monoester compound of Formula (I-1) (m/z=332.9 ($C_{12}H_{15}O_9P$)) and the phosphate diester compound of Formula (II-1) (m/z=568.8 ($C_{44}H_{43}O_{22}P$)). It is also confirmed from the peaks at chemical shift (δ) from 0 to −2 ppm of a spectrum of $^{31}P$ NMR shown in FIG. 2 that the phosphate ester combination contained the phosphate monoester compound of Formula (I-1) and the phosphate diester compound of Formula (II-1) and did not contain byproducts such as pyrophosphate and polyphosphate.

Example 1: Preparation of a Polyester Resin

Into a reactor (1 L) were added terephthalic acid (345.8 g, 2.083 mol) and ethylene glycol (161.49 g, 2.605 mol), which were then subjected to an esterification reaction at a temperature of 260° C. and at a nitrogen atmosphere of 2 kg/cm² until a conversion rate of at least 80% was achieved. A dispersion of the stabilizer (which was previously prepared by dispersing the stabilizer (0.034 g) prepared in Preparation Example 1 in ethylene glycol) and antimony (III) oxide ($Sb_2O_3$, 300 ppm) were added into the reactor to obtain a mixture. The mixture was then subjected to a polycondensation reaction at a temperature ranging from 270 to 275° C. for a period of 135 minutes to obtain a polyester resin containing a theoretic phosphorus content of 11.14 ppm.

Example 2: Preparation of a Polyester Resin

The procedure of Example 1 was repeated except that the amount of the stabilizer used in this example was 0.067 g. A polyester resin containing a theoretic phosphorus content of 22.14 ppm was obtained accordingly.

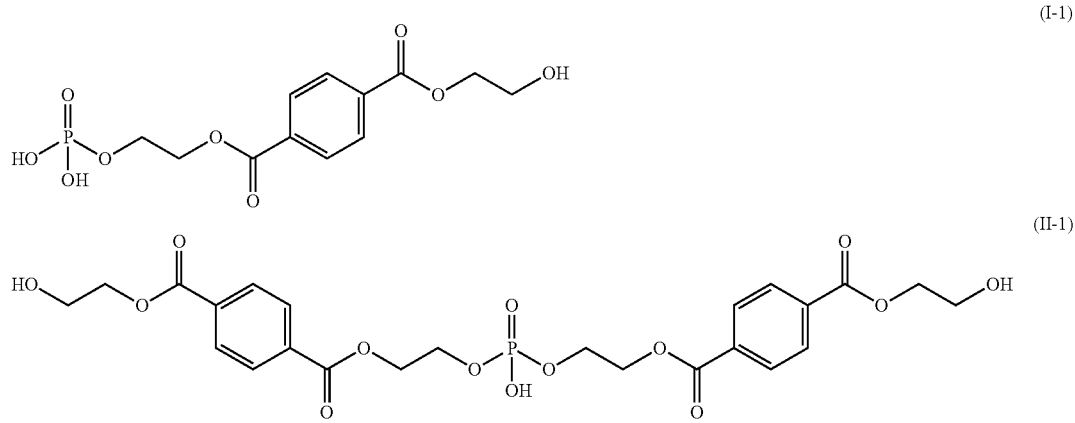

Example 3: Preparation of a Polyester Resin

The procedure of Example 1 was repeated except that the amount of the stabilizer used in this example was 0.087 g and that the polycondensation reaction was performed for a period of 140 minutes. A polyester resin containing a theoretic phosphorus content of 28.50 ppm was obtained accordingly.

Example 4: Preparation of a Polyester Resin

The procedure of Example 1 was repeated except that the amount of the stabilizer used in this example was 0.20 g and that the polycondensation reaction was performed for a period of 145 minutes. A polyester resin containing a theoretic phosphorus content of 65.80 ppm was obtained accordingly.

Example 5: Preparation of a Polyester Resin

The procedure of Example 1 was repeated except that the amount of the stabilizer used in this example was 0.40 g and that the polycondensation reaction was performed for a period of 150 minutes. A polyester resin containing a theoretic phosphorus content of 131.60 ppm was obtained accordingly.

Comparative Example 1: Preparation of a Polyester Resin

The procedure of Example 1 was repeated except that phosphoric acid (50 ppm) was used instead of the stabilizer prepared in Preparation Example 1 and that the polycondensation reaction was performed for a period of 155 minutes. A polyester resin containing a theoretic phosphorus content of 15.8 ppm was obtained accordingly.

Comparative Example 2: Preparation of a Polyester Resin

The procedure of Example 1 was repeated except that phosphoric acid (110 ppm) was used instead of the stabilizer prepared in Preparation Example 1 and that the polycondensation reaction was performed for a period of 167 minutes. A polyester resin containing a theoretic phosphorus content of 34.8 ppm was obtained accordingly.

Comparative Example 3: Preparation of a Polyester Resin

The procedure of Example 1 was repeated except that the stabilizer prepared in Preparation Example 1 was not used and that the polycondensation reaction was performed for a period of 120 minutes. A polyester resin was obtained accordingly.

Example 6: Preparation of a Polyester Resin

Into a reactor (5 L) were added terephthalic acid (2161.5 g, 13.021 mol) and ethylene glycol (1009.1 g, 16.276 mol), which were then subjected to an esterification reaction at a temperature of 260° C. and at a nitrogen atmosphere of 2 kg/cm$^2$ until a conversion rate of at least 80% was achieved. A dispersion of the stabilizer (which was previously prepared by dispersing the stabilizer (0.300 g) prepared in Preparation Example 1 in ethylene glycol) and antimony (III) oxide ($Sb_2O_3$, 300 ppm) were added into the reactor to obtain a mixture. The mixture was then subjected to a polycondensation reaction at a temperature ranging from 270 to 275° C. for a period of 240 minutes to obtain a polyester resin containing a theoretic phosphorus content of 15.8 ppm.

Example 7: Preparation of a Polyester Resin

The procedure of Example 6 was repeated except that the amount of the stabilizer used in this example was 0.570 g and that the polycondensation reaction was performed for a period of 250 minutes. A polyester resin containing a theoretic phosphorus content of 30.0 ppm was obtained accordingly.

Example 8: Preparation of a Polyester Resin

The procedure of Example 6 was repeated except that the amount of the stabilizer used in this example was 0.854 g and that the polycondensation reaction was performed for a period of 248 minutes. A polyester resin containing a theoretic phosphorus content of 45.0 ppm was obtained accordingly.

Comparative Example 4: Preparation of a Polyester Resin

The procedure of Example 6 was repeated except that phosphoric acid (50 ppm) was used instead of the stabilizer prepared in Preparation Example 1 and that the polycondensation reaction was performed for a period of 220 minutes. A polyester resin containing a theoretic phosphorus content of 15.8 ppm was obtained accordingly.

Comparative Example 5: Preparation of a Polyester Resin

The procedure of Example 6 was repeated except that triethyl phosphate (TEP, 92.84 ppm) was used instead of the stabilizer prepared in Preparation Example 1 and that the polycondensation reaction was performed for a period of 250 minutes. A polyester resin containing a theoretic phosphorus content of 15.8 ppm was obtained accordingly.

Property Evaluation:
1. Intrinsic Viscosity (IV):

The polyester resin obtained in each of Examples 1 to 8 and Comparative Examples 1 to 5 was molten, discharged into a water bath to solidify, and pelletized using a pelletizer to obtain polyester pellets. The polyester pellets were added with a mixture of phenol and tetrachloroethane in a weight ratio of 3:2 to prepare a test solution of 0.4 wt/vol %. The intrinsic viscosity of the test solution was measured using an Ubbelohde viscometer at a temperature of 30±0.2° C. The higher the intrinsic viscosity, the more complete the polycondensation reaction. The results are shown in Tables 1 and 2 below.

2. Color Hue (L, $L_b$)

The polyester resin obtained in each of Examples 1 to 8 and Comparative Examples 1 to 5 was molten, discharged into a water bath to solidify, and pelletized using a pelletizer to obtain polyester pellets. The color hue (L, $L_b$) of the polyester pellets was measured using a color meter (NE4000, Nippon Denshoku Company). The larger the L value, the higher the whiteness of the polyester resin. When the $L_b$ value is positive, the larger the $L_b$ value, the more yellow the polyester resin. When the $L_b$ value is negative, the smaller the $L_b$ value, the more blue the polyester resin. It is desirable to have the $L_b$ value to approximate 0. The L value in a range from 60 to 75 and the $L_b$ value in a range from 3 to 10 are acceptable in the polyester resin industry. The results are shown in Tables 1 and 2 below.

3. Acid Value:

The polyester resin obtained in each of Examples 1 to 8 and Comparative Examples 1 to 5 was molten, discharged into a water bath to solidify, and pelletized using a pelletizer to obtain polyester pellets. The acid value ([COOH], meg/Kg) of the polyester pellets was measured using an acid value analyzer. The higher the acid value, the more incomplete the polycondensation reaction or the more the broken ester bonds in the polyester resin. The results are shown in Tables 1 and 2 below.

4. Solid State Polymerization Rate:

The polyester resin obtained in each of Examples 6 to 8 and Comparative Examples 4 and 5 was pre-crystallized and baked at a temperature of 140° C. to obtain polyester pellets. The polyester pellets were subjected to a solid state polymerization reaction at a temperature of 230° C. for a period of 6 hours. The products obtained at the reaction periods of 2, 4, and 6 hours are respectively measured for the intrinsic viscosities thereof. The results are shown in Table 3 below.

5. Thermal Stability:

The polyester resin obtained in each of Examples 6 to 8 and Comparative Examples 3 to 5 was pre-crystallized and baked at a temperature of 140° C. to obtain polyester pellets. The polyester pellets were heated in an oven at a temperature of 225° C. for 1 hour. Thereafter, the intrinsic viscosity, the acid value, the color hue, and the BB % value (broken bonds of ester bonds) of the polyester resin were measured. The BB % value was determined according to a formula below. The smaller the BB % value, the less the number of broken ester bonds in the polyester resin and the higher the thermal stability of the polyester resin. Details thereof may be found in *J. Appl. Polym. Sci.*, 1991, 42, 1041.

$$BB\% \text{ value} = 0.245 \times (\eta_1^{-1.47} - \eta_2^{-1.47})$$

wherein $\eta_1$ is an intrinsic viscosity of the polyester resin after heating, and $\eta_2$ is an intrinsic viscosity of the polyester resin before heating.

6. Theoretic Phosphorus Content and Practical Phosphorus Content:

The theoretic phosphorus content of the polyester resin obtained in each of Examples 1 to 8 and Comparative Examples 1 to 5 was determined according to a formula below. The practical phosphorus content of the polyester resin obtained in each of Examples 1 to 8 and Comparative Examples 1 to 5 was measured using an inductively coupled plasma optical emission spectrometer (ICP-OES, Perkin-2100).

$$\text{Theoretic phosphorus content (ppm)} = [(A \times B \times 10^{-2})/W] \times 10^6$$

wherein

A: amount of the stabilizer, g;

B: ratio of phosphorus in the stabilizer, wt %; and

W: total weight of the polyester resin, g.

TABLE 1

| | | Stabilizer | Theoretic Phosphorus Content (ppm) | Practical Phosphorus Content (ppm) | IV (dl/g) | Color Hue L | Color Hue $L_b$ | [COOH] (meq/Kg) | Reaction Period (mins) |
|---|---|---|---|---|---|---|---|---|---|
| Ex. | 1 | Prep. Ex. 1 | 11.14 | 8.6 | 0.695 | 60.7 | 9.2 | 26.4 | 135 |
| | 2 | | 22.14 | 19.4 | 0.698 | 61.0 | 5.8 | 23.7 | 135 |
| | 3 | | 28.50 | 24.7 | 0.694 | 59.3 | 5.3 | 18.6 | 140 |
| | 4 | | 65.80 | 60.6 | 0.619 | 68.8 | 6.4 | 23.5 | 145 |
| | 5 | | 131.60 | 102.3 | 0.630 | 71.2 | 5.7 | 18.2 | 150 |
| Comp. | 1 | $H_3PO_4$ | 15.8 | 13.6 | 0.683 | 65.6 | 6.7 | 9.5 | 155 |
| Ex. | 2 | $H_3PO_4$ | 34.8 | 32.5 | 0.660 | 67.9 | 7.7 | 16.0 | 167 |
| | 3 | — | 0 | 0 | 0.673 | 70.2 | 8.2 | 21.4 | 120 |

TABLE 2

| | | Stabilizer | Theoretic Phosphorus Content (ppm) | Practical Phosphorus Content (ppm) | IV (dl/g) | Color Hue L | Color Hue $L_b$ | [COOH] (meq/Kg) | Reaction Period (mins) |
|---|---|---|---|---|---|---|---|---|---|
| Ex. | 6 | Prep. Ex. 1 | 15.8 | 11.8 | 0.613 | 54.8 | 2.9 | 14.2 | 240 |
| | 7 | | 30.0 | 20.7 | 0.605 | 59.2 | 2.4 | 13.5 | 250 |
| | 8 | | 45.0 | 33.4 | 0.605 | 64.9 | 3.9 | 13.7 | 248 |
| Comp. | 4 | $H_3PO_4$ | 15.8 | 15.6 | 0.609 | 59 | 2.3 | 16.5 | 220 |
| Ex. | 5 | TEP | 15.8 | 5.3 | 0.607 | 55 | 2.5 | 15.5 | 250 |

TABLE 3

| | | | Intrinsic Viscosity (IV) (dl/g) | | | |
|---|---|---|---|---|---|---|
| | | Stabilizer | Before SSP | SSP 2 hours | SSP 4 hours | SSP 6 hours |
| Ex. | 6 | Prep. Ex. 1 | 0.613 | 0.673 | 0.700 | 0.715 |
| | 7 | | 0.605 | 0.623 | 0.668 | 0.706 |
| | 8 | | 0.605 | 0.622 | 0.664 | 0.705 |
| Comp. | 4 | $H_3PO_4$ | 0.609 | 0.650 | 0.674 | 0.693 |
| Ex. | 5 | TEP | 0.607 | 0.633 | 0.675 | 0.688 |

TABLE 4

| | | Stabilizer | After heating at 225° C. for 1 hour | | | | | | |
|---|---|---|---|---|---|---|---|---|---|
| | | | IV (dl/g) | $L_b$ | [COOH] (meq/Kg) | ΔIV (dl/g) | Δ[COOH] (meq/Kg) | $ΔL_b$ | BB % |
| Ex. | 6 | Prep. Ex. 1 | 0.519 | 1.7 | 68.5 | −0.094 | 54.3 | −1.2 | 0.139 |
| | 7 | | 0.489 | 2.0 | 69.4 | −0.116 | 55.9 | −0.4 | 0.188 |
| | 8 | | 0.503 | 3.8 | 61.3 | −0.102 | 47.6 | −0.1 | 0.160 |
| Comp. | 3 | — | 0.497 | 8.5 | 93.2 | −0.176 | 71.8 | 0.3 | 0.246 |
| Ex. | 4 | $H_3PO_4$ | 0.463 | 3.9 | 75.8 | −0.146 | 59.3 | 1.6 | 0.252 |
| | 5 | TEP | 0.458 | 2.6 | 90.2 | −0.149 | 74.7 | 0.1 | 0.262 |

From the theoretical phosphorus contents, it can be seen that the acid values, and the reaction periods of Examples 1 to 5 shown in Table 1, the rate of the polycondensation reaction for preparing the polyester resin are not substantially affected by the amount of the stabilizer prepared in Preparation Example 1, indicating that the yield of the polyester resin is not significantly affected by the amount of the stabilizer prepared in Preparation Example 1. From the color hue values shown in Table 1, it is shown that the color hue values of the polyester resins obtained in Examples 1 to 5 meet the requirements of the polyester resin industry, demonstrating that the stabilizer of the disclosure can avoid degradation of the polyester resin during the polycondensation reaction to permit the molecular weight and the color hue of the polyester resin thus produced to meet the requirements of the polyester resin industry, and that the stabilizer of the disclosure would not undesirably affect the production rate and the yield of the polyester resin.

From the theoretical phosphorus contents, the acid values, and the reaction periods of Comparative Examples 1 and 2 shown in Table 1, it can be seen that although degradation of the polyester resin during the polycondensation reaction caused by the presence of the catalyst may be avoided when phosphoric acid was used as a stabilizer, the production rate of the polyester resin would be inhibited with the increased amount of phosphoric acid used, indicating that the production rate and the yield of the polyester resin may be undesirably affected by the amount of phosphoric acid used.

As shown in Tables 2 and 3, in Examples 6 to 8 in which the stabilizer prepared in Preparation Example 1 was used, the polyester resins obtained after 6 hours of the solid state polymerization reaction have an intrinsic viscosity of at least 0.7. However, in Comparative Examples 4 and 5 in which phosphoric acid and triethyl phosphate (i.e., a phosphate triester) were used, respectively, the polyester resins obtained after 6 hours of the solid state polymerization reaction have an intrinsic viscosity of less than 0.7. It is demonstrated that the stabilizer of the disclosure, which includes a combination of phosphate monoester and phosphate diester, may more effectively enhance the reaction rate of the sol id state polymerization reaction compared to both phosphoric acid and phosphate triester.

As shown in Table 4, in Examples 6 to 8 in which the stabilizer prepared in Preparation Example 1 was used, the intrinsic viscosity variation (i.e., ΔIV), the acid value variation (i.e., Δ[COOH]), the color hue variation (i.e., ΔLb), and the BB % value of the polyester resins after the heating treatment are relatively small, indicating that the polyester resins obtained in Examples 6 to 8 have relatively superior thermal stability. However, in Comparative Examples 3 to 5, the intrinsic viscosity variation (i.e., ΔIV), the acid value variation (i.e., Δ[COOH]), the color hue variation (i.e., ΔLb), and the BB % value of the polyester resins after the heating treatment are relatively large, indicating that the polyester resins obtained in Comparative Examples 3 to 5 have relatively inferior thermal stability. It is demonstrated that the stabilizer of the disclosure, which includes a combination of phosphate monoester and phosphate diester, may more effectively enhance the thermal stability of the polyester resin thus produced compared to both of phosphoric acid and phosphate triester.

In a conventional procedure of processing a polyester resin, the polyester resin is generally first processed into polyester pellets, which are then further processed into a formed article such as a bottle, a plate, and the like. Due to a heating treatment in the further processing, the BB % value of the polyester resin will be raised. The heating treatment (i.e. heating at 225° C. for 1 hour) shown in Table 4 is to simulate the further processing for the polyester resin in the conventional procedure. As shown in Table 4, in Examples 6 to 8 in which the stabilizer prepared in Preparation Example 1 was used, the increase of the BB % value of the polyester resin in the further processing may be effectively inhibited.

In view of the aforesaid, use of the stabilizer of the disclosure in producing a polyester resin may avoid degradation of the polyester resin in the polycondensation reaction. The polyester resin thus produced may have a molecular weight and a color hue which may meet the requirements of the polyester resin industry. At the same time, the stabilizer of the disclosure may not undesirably affect the production rate and the yield of the polyester resin, and may enhance the reaction rate of the polyester resin in the solid state polymerization reaction and the thermal stability of the polyester resin in the further processing of the polyester resin into an a formed article.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A stabilizer for producing a polyester resin, comprising a phosphate ester composition which includes a phosphate ester compound having Formula (I),

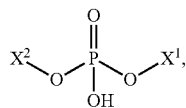 (I)

wherein
X¹ represents

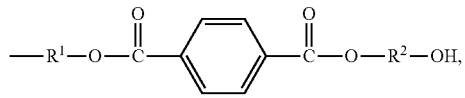

and
X² represents H or

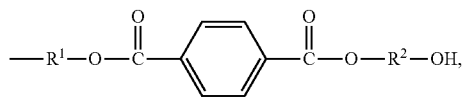

wherein
R¹ and R² are independently selected from the group consisting of a linear $C_2$-$C_4$ alkylene group, a branched $C_3$-$C_4$ alkylene group, and a combination thereof.

2. The stabilizer according to claim 1, wherein said phosphate ester composition includes the phosphate ester compound having Formula (I) wherein X² is H.

3. The stabilizer according to claim 2, wherein said phosphate ester composition further includes the phosphate ester compound having Formula (I) wherein X² is

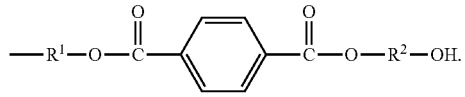

4. The stabilizer according to claim 3, wherein the phosphate ester compound having Formula (I) wherein X² is H and the phosphate ester compound having Formula (I) wherein X² is

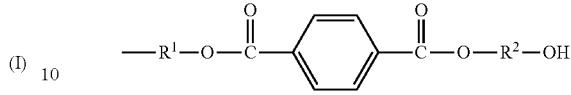

are in an equivalent ratio ranging from 1:1 to 9:1.

5. A process for preparing the stabilizer according to claim 1, comprising steps of:
 a) dispersing phosphorus pentoxide in a solvent to obtain a phosphorus pentoxide dispersion; and
 b) subjecting a compound having Formula (A) to a phosphorylation reaction with the phosphorus pentoxide at a temperature ranging from 40° C. to 100° C. by gradually adding the compound having Formula (A) into the phosphorus pentoxide dispersion,

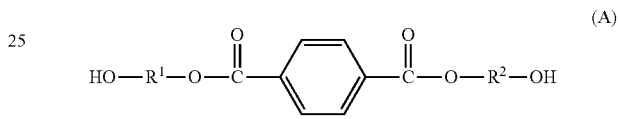 (A)

wherein
R¹ and R² are independently selected from the group consisting of a linear $C_2$-$C_4$ alkylene group, a branched $C_3$-$C_4$ alkylene group, and a combination thereof.

6. The process according to claim 5, wherein in step b), the phosphorus pentoxide and the compound having Formula (A) are in a molar ratio ranging from 1:1 to 1:2.

7. A process for producing a polyester resin, comprising a step of:
 subjecting a dicarboxylic ester component to a polycondensation reaction in the presence of a catalyst and the stabilizer according to claim 1.

8. The process according to claim 7, wherein the stabilizer is used in an amount such that the polyester resin thus produced contains a practical phosphorus content in a range from 5 ppm to 150 ppm.

9. The process according to claim 7, wherein the catalyst is a metal-containing catalyst.

10. A polyester resin produced by the process according to claim 7.

* * * * *